(12) United States Patent
Decroux et al.

(10) Patent No.: US 9,702,833 B2
(45) Date of Patent: Jul. 11, 2017

(54) DEVICE AND METHOD FOR THE NONDESTRUCTIVE TESTING OF TIRES BY TOMOGRAPHY

(71) Applicant: CyXplus, Marseilles (FR)

(72) Inventors: Agnès Decroux, Lumbin (FR); Fabrice Ficalora, Les Pennes Mirabeau (FR); Olivier Roubaud, Trets (FR); Olivier Francois, Villard-Bonnot (FR)

(73) Assignee: CyXplus (FR)

( * ) Notice: Subject to any disclaimer, the term of this patent is extended or adjusted under 35 U.S.C. 154(b) by 85 days.

(21) Appl. No.: 14/765,598

(22) PCT Filed: Feb. 4, 2014

(86) PCT No.: PCT/FR2014/050198
§ 371 (c)(1),
(2) Date: Aug. 4, 2015

(87) PCT Pub. No.: WO2014/118482
PCT Pub. Date: Aug. 7, 2014

(65) Prior Publication Data
US 2015/0377802 A1   Dec. 31, 2015

(30) Foreign Application Priority Data
Feb. 4, 2013   (FR) ...................................... 13 50955

(51) Int. Cl.
*G01N 23/02*   (2006.01)
*G01N 23/18*   (2006.01)
(Continued)

(52) U.S. Cl.
CPC ........ *G01N 23/185* (2013.01); *G01M 17/028* (2013.01); *G21K 1/02* (2013.01); *G01N 2223/627* (2013.01)

(58) Field of Classification Search
CPC .. G01N 23/185; G01N 2223/627; G21K 1/02; G01M 17/028
(Continued)

(56) References Cited

U.S. PATENT DOCUMENTS 5,027,378 A * 6/1991 Fujii ................... G01N 23/046
378/10

FOREIGN PATENT DOCUMENTS

EP   0 471 096 A1   2/1992
JP   H02 195237   8/1990

OTHER PUBLICATIONS

International Search Report dated Jun. 24, 2014 issued in corresponding International patent application No. PCT/FR2014/050198.
(Continued)

*Primary Examiner* — Courtney Thomas
(74) *Attorney, Agent, or Firm* — Ostrolenk Faber LLP

(57) ABSTRACT

A device for testing a tyre (2) for representing tomographical images of sections of a casing of the tyre includes a source (11) of ionizing radiation arranged outside the tyre (2) and a detector (12) for receiving the radiation. The detector (12) is situated opposite the source (11) with respect to at least one section of the casing. The axis (X-X) of the tyre runs parallel to a sectional plane (P) passing through the focus (F) of the source (11) and the detector (12). The tyre and the source-detector assembly are moved with rotational motion relative to one another about an axis of rotation (Z-Z) perpendicular to the sectional plane (P), according to a predetermined angular excursion range. The detector (12) is disposed in a central internal zone (20) of the tyre (2) during the testing cycle.

15 Claims, 7 Drawing Sheets

(51) Int. Cl.
*G01M 17/03* (2006.01)
*G21K 1/02* (2006.01)

(58) Field of Classification Search
USPC .................................................. 378/58, 61
See application file for complete search history.

(56) References Cited

OTHER PUBLICATIONS

Written Opinion dated Jun. 24, 2014 issued in corresponding International patent application No. PCT/FR2014/050198.
International Preliminary Report on Patentability dated Feb. 25, 2015 issued in corresponding International patent application No. PCT/FR2014/050198.

* cited by examiner

DEVICE AND METHOD FOR THE NONDESTRUCTIVE TESTING OF TIRES BY TOMOGRAPHY

CROSS-REFERENCE TO RELATED APPLICATIONS

The present application is a 35 U.S.C. §§371 national phase conversion of PCT/FR2014/050198, filed Feb. 4, 2014, which claims priority of French Patent Application No. 1350955, filed Feb. 4, 2013, the contents of which are incorporated by reference herein. The PCT International Application was published in the French language.

The present invention relates to a tomographic inspection method based on X-ray exploration of a tire, with a view to a non-destructive inspection of its internal structure. It relates also to a device for implementing this method. The method and the device allow for the representation of tomographic images of slices of tires.

As is known, obtaining a tomographic image of a section of an object using a tomographic apparatus including a source-detector assembly comprises emitting a beam of incident X-rays toward this object, while the detector measures the absorption of the X-rays passing through the object. The absorption is linked to the density of the materials constituting the object being studied. A multiplicity of scans in known and controlled directions makes it possible to know, after an appropriate digital processing of the signals collected on the detection cells of the detector, the value of the absorption of the X-rays at each point of the sectional plane considered, and thus to know the density of the materials constituting the object. The knowledge of the different values of this density makes it possible to reconstruct the image of the section of the object.

A known device for inspecting tires by X-ray tomography was developed by the company Yxlon and marketed under the reference "Y.CT Tire". This device comprises an X-ray tube and a linear detector arranged on either side of the side walls of a tire, brought into a vertical position between the source and the detector, so as to obtain three-dimensional views in radial cross section of the cover of the tire, by the rotation of the tire about a vertical axis. However, this device is arranged to make it possible to inspect tires which are mounted on a rim and inflated, and which must be entirely positioned between the source and the detector. This device is used for research and development purposes to analyze the behavior of a tire under load. However, it is not suited to systematic inspection during manufacture. In effect, in addition to the fact that the radiography acquisition time is very long, the emission of X-rays has to be performed with high energy to be able to pass through the metal, to the detriment of the information concerning the rubber of which the tire is made. Consequently, the radiation energy used is too high to make it possible to correctly visualize, on the one hand, the rubber constituting the cover of the tire and, on the other hand, the positioning of the metal plies in the rubber. In other words, only the metal plies constituting the cover of the tire are visible on the images produced.

Moreover, the document EP0471096A1 discloses a device for inspecting tires by X tomography in which only half of the tire is arranged between the source and the detector, and the detector penetrates inside the tire during the inspection cycle. This solution presents the advantage of requiring X-rays of lower energy, which improves the quality of the images obtained, and notably the contrast between the metal and polymer components. However, this device does present a number of drawbacks. First, the inspection of a tire is slow because it requires numerous cycles of relative displacements between, on the one hand, the source-detector assembly and, on the other hand, the tire. These relative displacements sequentially comprise round trips along a transverse rectilinear axis and angular increments according to a rotational movement. Furthermore, when this device is used to inspect tires of substantially different sizes, these relative displacement cycles have to be modified, which complicates and extends the parameterizing and the setting up of the device upon a change of tire size.

SUMMARY OF THE INVENTION

In this context, the aim of the present invention is to propose a device and a method for inspecting tires by tomography, free of at least one of the limitations described previously and, in particular, which make it possible, with a reduced cycle time, to reconstruct tomography images exhibiting an enhanced contrast between the metal plies and the polymeric layers constituting the cover of the tire and which further make it possible to cover a wide range of tire sizes by simplifying the settings upon changes of size.

In order to resolve this problem, the present invention proposes a device for inspecting a tire, intended to allow for the representation of tomographic images of sections of a cover of said tire, comprising a source of ionizing radiation arranged outside of said tire suitable for emitting the radiation in the form of a divergent beam and a detector suitable for receiving said radiation after passing through at least a part of said tire. The detector is arranged facing said source at a predetermined distance L2 from said source and is situated opposite said source relative to at least one cover section of said tire. The tire is held between the source and the detector with the axis of the tire extending parallel to a sectional plane passing through the focus of said source and said detector, wherein the tire and the source-detector assembly are suitable for being moved by a rotational movement relative to one another about an axis of rotation at right angles to the sectional plane and the intersection with said sectional plane passes through a center of rotation situated between said source and said detector at a predetermined distance L1 from the source. The device is arranged such that, during an inspection cycle, said detector is arranged at least partly in a central internal zone of said tire. According to the invention, the intersection of the divergent beam with the sectional plane exhibits an angular aperture of between 13° and 30°, whereas said center of rotation is positioned in a fixed manner between said source and said detector such that the ratio L1/L2 is between 0.75 and 0.9, so that said device is suitable for inspecting tires of different dimensions by keeping constant the relative positions of said source, of said detector and of said center of rotation.

By virtue of this arrangement, given that the detector passes inside the central internal zone of the tire during an inspection cycle, the tire is only partially positioned between the source and the detector. In this case, on each firing performed from the source of radiation, the section of cover opposite to that tomographied relative to the axis of the tire, never passes through the field of radiation acquired by the detector. The reconstruction of the tomographic image produced is therefore not polluted by the section of cover opposite the one tomographied. Furthermore, the fact that the tomography produced relates to a single section of cover simultaneously makes it possible to limit the radiation energy and thus to augment the contrast of the reconstructed image, while advantageously reducing the cost of the associated radioprotection means. Finally, the relative movement of the tire and of the source-detector assembly about an axis of rotation at right angles to said sectional plane makes it possible to modify the relative positioning of the tire and of the source-detector assembly over a given angular excursion range and thereby perform multiple scans of the section of cover to be tomographied by modifying, on each scan, the angular position of the section of cover relative to said sectional plane in a reduced cycle time.

Furthermore, it has been discovered that the particular combination of an angular aperture of the beam of between 13° and 30° with a center of rotation positioned in a fixed manner between the source and the detector according to the criterion L1/L2 of between 0.75 and 0.9 made it possible to be able to perform the inspection of a wide range of tires of different dimensions without requiring complex adjustments on each change of dimensions. In effect, to obtain an accurate tomographic reconstruction, the reconstruction algorithm has to be calibrated in order notably to accurately determine the exact position of the axis of rotation of the inspected object relative to the source and to the detector. This calibration is a lengthy operation which requires the inspection of a reference part of perfectly known geometry, and complex computations to deduce from the recorded signals the exact position of the axis of rotation. Now, the present invention makes it possible to not have to modify the position of the axis of rotation, even to inspect tires of very different sizes, for example tires of outer diameter varying almost from single to double, which makes it possible to dispense with this calibration upon a change of tire size.

What is more, the range of angular aperture chosen is compatible with a reconstruction algorithm of Feldkamp type, this type of algorithm offering the advantages of being robust, rapid and well suited to real-time processing. The speed of inspection is thus improved relative to that of the devices of the prior art, notably relative to that of the device disclosed by the document EP0471096A1, because, during the inspection, the only relative displacement between, on the one hand, the source-detector assembly and, on the other hand, the tire, is a simple rotational movement.

According to other advantageous features of the device according to the invention, taken in isolation or in combination:

said center of rotation is situated inside said section of cover of said tire;
the angular aperture of the divergent beam is advantageously between 15° and 25°;
the ratio L1/L2 is advantageously between 0.8 and 0.9;
the length L2 is advantageously less than 2 meters, more advantageously less than 1.5 meters, preferentially between 1.1 meters and 1.4 meters;
the source of ionizing radiation is a source of X-rays;
said source of ionizing radiation is preferably an X-ray tube of a voltage less than 250 kV; thus, the device of the invention makes it possible to use a much lower radiation energy than the device of the prior art described above. In effect, the latter uses a significantly higher energy radiation source, namely an X-ray tube or a voltage of the order of 450 kV, or even a linear accelerator (LINAC) that is even more energy intensive, so as to be able to pass through all of the tire mounted on its metal rim, with the disadvantage of loss of information on the less dense materials constituting the tire. By contrast, an X-ray tube of a voltage less than 250 kV emits low energy X photons, which makes it possible to improve the tomographic inspection of the components of the tire exhibiting a low density (i.e. polymers, rubber), while remaining sufficient to pass through a section of cover of a tire of a private passenger or truck type vehicle. In effect, given that, according to the invention, the radiation must pass through only half of the tire (i.e. only one of the two sections of cover), it is possible and advantageous to reduce the energy of the X photons of the radiation;
said detector can be a linear or matrix detector;
the relative rotational movement between said source-detector assembly and said tire is advantageously a continuous movement;
said device preferentially comprises means for rotationally driving said tire about said axis of rotation over said angular excursion range;
as a variant, said device comprises means for rotationally driving the source-detector assembly about said axis of rotation over said angular excursion range;
said tire is preferably arranged such that the axis of said tire belongs to said sectional plane passing through the focus of said source and said detector; the sectional plane is then radial relative to the tire, which makes it possible to obtain a radial tomographic section. Such a section makes it possible to replace the examinations of samples taken radially, according to the current destructive inspection practice;
said angular excursion range preferentially extends over at least 180°;
said device advantageously comprises means for rotationally driving said tire about its axis;
said source is preferably equipped with a collimator such that the radiation is emitted in the form of a planar beam contained in said sectional plane; such a collimator is a device known to be suited to the radiation source, so as to obtain a planar fan beam. Advantageously, the thickness of the beam measured at the detector is less than 30 mm, preferably less than 20 mm. The use of such a collimator advantageously makes it possible to reduce needs for radio-protection in the inspection chamber and further provides a better result because of the reduction of the noise linked to the scattering of the plastic materials. With the use of a collimator, this variant is further particularly advantageous taken in combination with the use of a detector of linear detector type positioned also in said sectional plane;
said tire is preferably held in the vertical position and said sectional plane is horizontal;
as a variant, said tire is held in the horizontal position and said sectional plane is vertical.

The invention relates also to a method for inspecting a tire intended to allow for the representation of tomographic images of sections of a cover of said tire, in which:

a tire, a source of ionizing radiation intended to emit a radiation to said tire in the form of a divergent beam and a detector aligned with said source at a predetermined distance L2 from said source are provided, such that said source and said detector are situated on either side of the cover of said tire, the axis of said tire extending parallel to a sectional plane passing through the focus of said source and said detector, during an inspection cycle, a relative rotational movement is generated between said tire and the source-detector assembly about an axis of rotation at right angles to said sectional plane and whose intersection with said sectional plane passes through a center of rotation situated between said source and said detector at a predetermined distance L1 from said source, while passing said detector, at least partly, inside a central internal zone of said tire during said rotational movement, and during said inspection cycle, said detector is used to measure the absorption of said radiation passing through at least one section of cover along said sectional plane, said method being characterized in that the intersection of said divergent beam with said sectional plane exhibits an angular aperture of between 13° and 30°, whereas said center of rotation is positioned in a fixed manner between said source and said detector such that the ratio L1/L2 is between 0.75 and 0.9, so that it is possible to inspect tires of different dimensions while keeping constant the relative positions of said source, of said detector and of said center of rotation.

Preferably, said tire is turned about said axis of rotation at right angles to said sectional plane.

As a variant, the source-detector assembly is turned about said axis of rotation at right angles to said sectional plane.

Said axis of rotation preferentially passes through a center of rotation situated inside said section of cover of said tire.

BRIEF DESCRIPTION OF THE DRAWINGS

Other features and advantages of the invention will become apparent on reading the following description of a particular embodiment of the invention, given by way of indication but in a nonlimiting manner, with reference to the attached drawings in which.

DESCRIPTION OF AN EMBODIMENT

Figure 1:
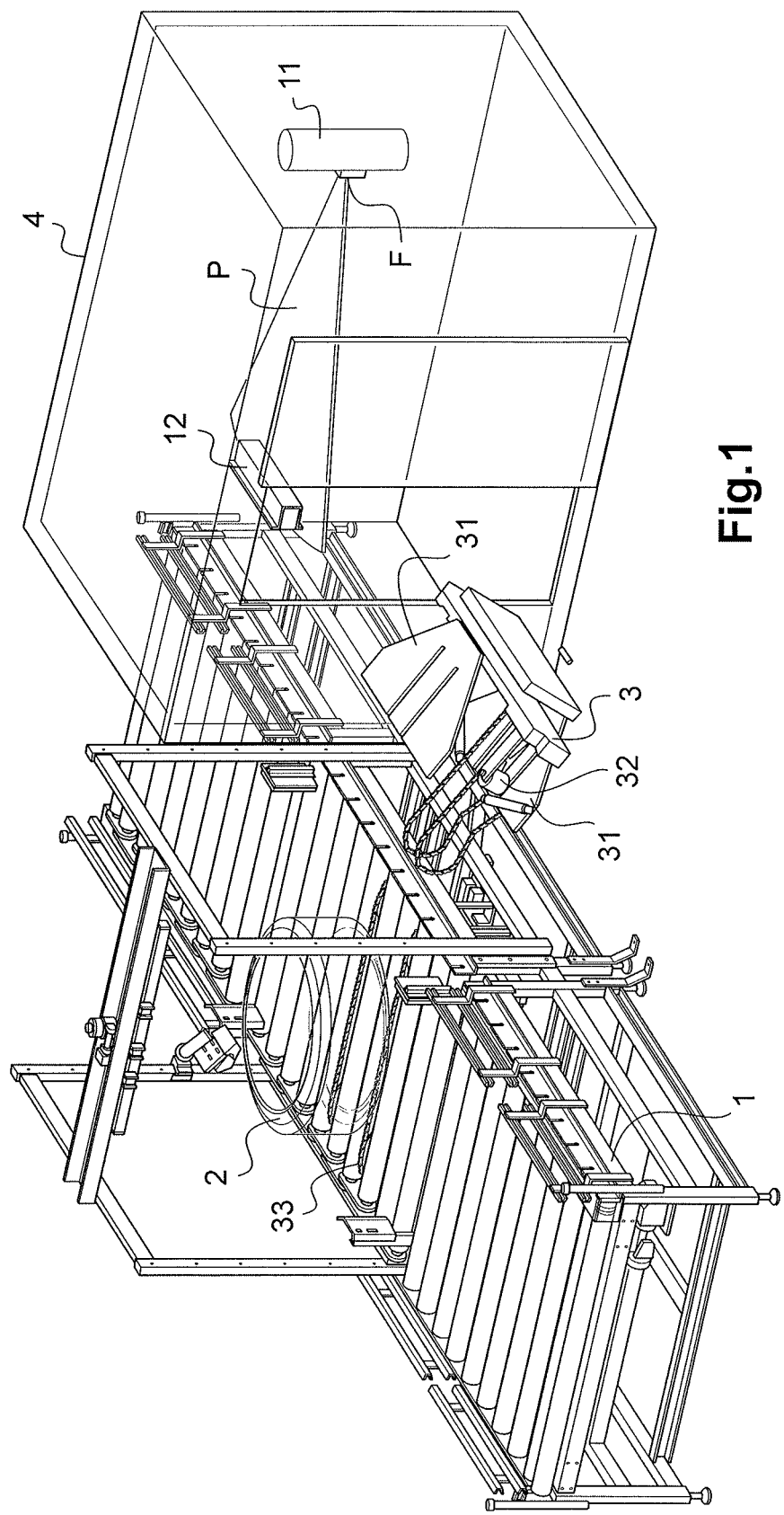
FIG. 1 is a perspective schematic view of a device according to the invention, with the cover of the tire in horizontal feed position.

The device according to the invention for inspecting tires by X-ray tomography is intended to be incorporated in a tire production line. A feed conveyor 1 for a tire 2 cooperates with a handling carriage 3 to transfer the tire 2 from the feed conveyor 1 to an inspection chamber 4, having walls impermeable to the X-rays, where an X-ray source 11 and an X-ray detector 12 are arranged. The detector 12 can be a linear or matrix detector and is arranged horizontally in the inspection chamber 4 facing the source 11. The source 11 is preferentially equipped with a collimator such that the radiation is emitted in the form of a flat beam of horizontal axis, defining a sectional plane P, also called firing plane, passing through the focus F of the source 11 and the detector 12, positioned horizontally.

Figure 2:
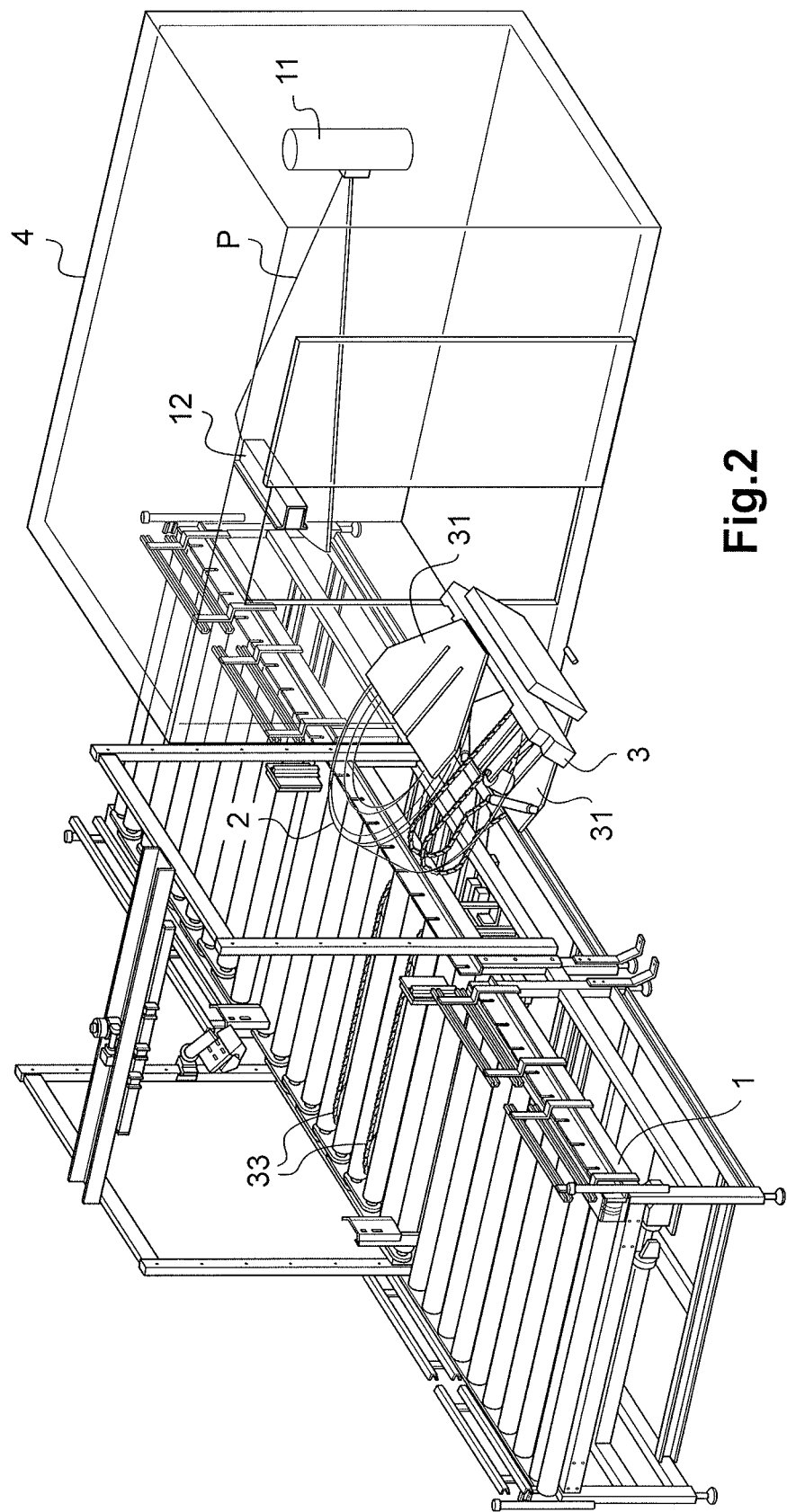
FIG. 2 is a perspective schematic view of a device according to the invention, with the cover of the tire during transfer to an inspection chamber.

The handling carriage 3 of the tire comprises a frame supporting a motor-drive system making it possible for the carriage 3 to be able to be displaced on a rail (not represented) arranged parallel to the longitudinal direction of the feed conveyor 1. In particular, the handling carriage 3 is suitable for being displaced along the rail of a zone for loading the tire 2 from the feed conveyor 1 to the interior of the inspection chamber 4. In the loading zone, the handling carriage 3 is arranged laterally to the feed conveyor 1, facing driving means 33 incorporated in the feed conveyor 1 and suitable for driving the tire 2, in the horizontal position on the feed conveyor, in a direction at right angles to the longitudinal direction of the feed conveyor 1. In this way, the tire 2, transported in the horizontal position on the feed conveyor 1, is loaded in this position into the handling carriage 3 (FIG. 2). The carriage 3 is provided with means for tilting the tire that is suitable for switching the tire from the horizontal loading position to a vertical position, in which it will be transferred via the carriage into the inspection chamber 4. These tilting means are also designed to allow the tire to be tilted from the vertical position to the horizontal position. After its loading, the tire 2 is therefore positioned vertically in the handling carriage 3. Furthermore, the handling carriage 3 is provided with means for holding the tire, enabling the tire 2 to be held vertically by means of a pressure exerted at the base of the tire positioned vertically in the carriage. These holding means comprise two jaws 31, arranged facing one another, between which the tire 2 is loaded and which are suitable for being applied against the respective side walls of the bottom part of the cover of the tire by exerting a pressure against them when the tire is in the vertical position. Furthermore, the handling carriage 3 is provided with means for adjusting the position of the tire 2 that is thus held in the carriage, for example implemented in the form of a system of rollers in contact with the bottom part of the tread of the tire, making it possible to ensure the centering of the tire on the carriage and its height relative to the base of the carriage. In particular, these means for adjusting the position of the tire make it possible to position the horizontal radial plane of the cover of the tire 2 at a height such that it coincides with the sectional plane P formed by the focus F of the source 11 and the detector 12, when the tire 2 is transferred into the inspection chamber 4. In other words, the axis X-X of the tire 2 should preferentially lie in the sectional plane P upon the implementation of a tire 2 inspection cycle. Finally, the handling carriage 3 of the tire also comprises means for rotationally driving the tire about its axis X-X, for example in the form of a motorized roller 32 in contact with the bottom part of the tread of the tire positioned vertically on the carriage. These means advantageously make it possible to turn the tire on itself in order to be able to present various angles of section of cover to be tomographied.

Figure 3:
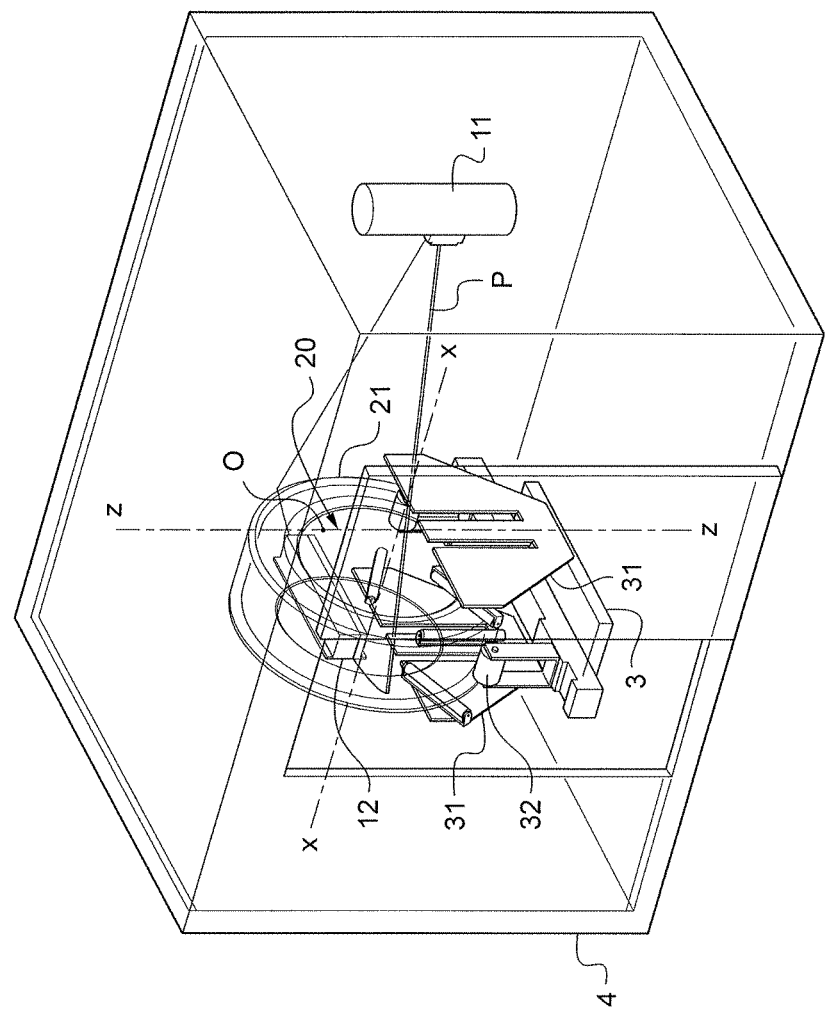
FIG. 3 is a perspective schematic view of a device according to a preferred embodiment of the invention, illustrating an input, respectively output, position of the tire in the inspection chamber for the implementation of an inspection cycle.

There now follows a more detailed description of the phase of acquisition of the X-ray images of a section of cover of the tire 2, implemented during a tire 2 inspection cycle. The phase of acquisition of the X-ray images is therefore performed in the inspection chamber 4, with the tire 2 held preferentially in the vertical position on the handling carriage 3 and positioned heightwise such that its axis X-X is situated in the horizontal sectional plane P passing through the focus F of the source 11 and the detector 12. Note that the tire 2 that is thus held and positioned is not mounted on a rim for the implementation of the inspection cycle. FIG. 3 illustrates the position of input of the tire 2 into the inspection chamber 4, in which the cover of the tire 2 is fed into immediate proximity of the detector 12 in the inspection chamber 4 and is positioned relative to the source-detector assembly, such that the axis X-X of the tire is substantially at right angles to the longitudinal axis of the detector 12, that is to say such that the side wall of the tire 2 is substantially parallel to the detector 12. In this position, the detector 12 is situated opposite the source 11 relative to the section of cover 21 to be tomographied.

In accordance with the invention, during the image acquisition phase, the detector 12 positioned horizontally is designed to move inside the central internal zone 20 of the tire 2, whereas the tire 2 and the source 11-detector 12 assembly are designed to be moved by a rotational movement relative to one another about an axis of rotation Z-Z at right angles to the sectional plane P, so as to be able to modify the angular position of the cover of the tire 2 relatively to the horizontal sectional plane P, over a predetermined angular excursion range, advantageously between 180° and 360°, and preferentially equal to 180°. Thus, given that the detector passes inside the central internal zone 20 of the tire, on each measurement acquired by the source-detector assembly, the beam intercepted by the detector 12 passes through a single section of cover, which is the one to be tomographied, and the section of cover opposite to the one tomographied (relative to the axis of the tire) never passes into the field of the radiation beam acquired by the detector 12. Furthermore, the beam intercepted by the detector after passing through the section of cover to be tomographied is wide enough to cover all of the section of cover. Moreover, the fact that only a single section of cover is irradiated makes it possible to maintain a close and relatively constant distance between the section of cover, the detector and the source, which has the effect of limiting the variations of enlargement in the acquired image. Also, the fact that only a single section of cover is irradiated means less energy is required, which makes it possible to increase the contrast of the reconstructed image and thus be able to view both the rubber and the positioning of the metal plies in the rubber.

According to a preferred embodiment, the source-detector assembly is designed to remain fixed, whereas the tire, preferentially positioned vertically, is driven in rotation about the vertical axis of rotation Z-Z, via rotational driving means. To do this, the handling carriage cooperates with a pivot mechanism making it possible to rotate the cover of the vertically positioned tire 2 about the vertical axis of rotation Z-Z. For example, the pivot mechanism ensuring the rotation of the cover of the tire about the vertical axis of rotation Z-Z consists of a horizontal revolving plate (not represented) cooperating with the base of the handling carriage and the tire 2 is positioned on the revolving plate via the handling carriage, such that the vertical axis of rotation of the horizontal revolving plate coincides with the axis of rotation Z-Z about which the cover of the tire 2 is to be rotated. The holding of the tire 2 in the vertical position on the handling carriage 3 via jaws 31 advantageously makes it possible to avoid having the tire move during the rotation of the revolving plate, which would have the effect of generating a significant blurring on the reconstructed tomographic images. Moreover, the rotational movement of the tire about the vertical axis of rotation Z-Z is preferentially a continuous movement during the inspection cycle, so as to reduce the duration of the cycle.

Advantageously, the vertical axis of rotation Z-Z is designed to pass through a fixed point O situated inside the section of cover 21 of the tire to be tomographied. It is not however vitally important to have a fixed center of rotation relative to the tire. In other words, the tire can move rotationally in the reference frame provided that, on each scan, the position of the tire relative to the center of rotation is accurately known. The image reconstruction processing is however made more complicated. Nor is it vitally important for the center of rotation to be situated inside the section of the cover to be tomographied, although this configuration facilitates the operation of rotating the tire over an angular excursion range about the vertical axis, typically 180°, by passing the detector 12 inside the central internal zone 20 of the tire, in particular for a detector having a long length.

In a variant embodiment, the relative rotational movement between the tire and the source-detector assembly is obtained by keeping the tire fixed, whereas the source-detector assembly is designed to rotate about the vertical axis of rotation Z-Z. However, this variant is more complex to implement mechanically compared to that where it is the tire which is driven in rotation about the axis Z-Z and not the source-detector assembly.

Figure 4:
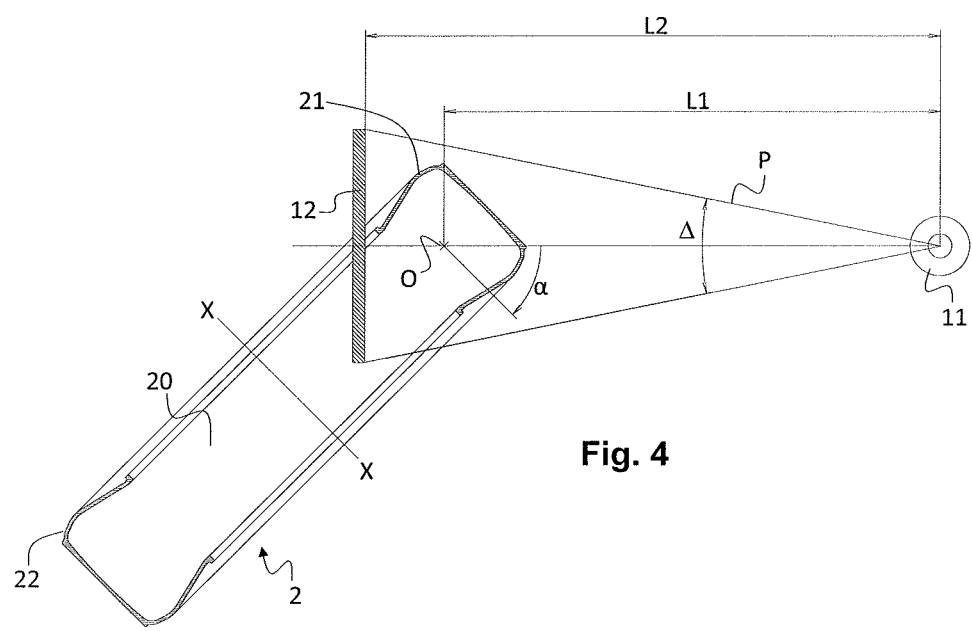
FIGS. 4-7 are schematic views from above of the source-detector assembly and of the tire, showing exemplary relative positions of the source-detector assembly and of the tire during a tire inspection cycle according to a preferred embodiment of the invention.

FIGS. 4 to 7 show examples of relative positions of the tire and of the source-detector assembly during a tire inspection cycle, obtained by rotating the tire about the vertical axis of rotation passing through the center of rotation O situated inside the section of cover 21 to be tomographied. Thus, FIG. 4 shows an initial position, where, because of the rotation of the tire 2, the detector 12 comes inside the tire 2 through its central internal zone 20, with an angle a considered between the axis X-X of the tire 2 and a line normal to the detector 12 passing through the focus F of the source, advantageously chosen between −45° and +45° and preferentially substantially equal to 45°. In this position, the detector 12 is situated opposite the source 11 relative to the section of cover 21 to be tomographied considered in the horizontal sectional plane P and the section of cover 22 opposite to the one tomographied 21 does not pass into the field of the radiation beam acquired by the detector 12.

The source 11 is equipped with a collimator such that the radiation is emitted in the form of a flat beam merged with the sectional plane P. This collimator is a device designed to be matched to the radiation source, so as to obtain a fan beam. This beam is advantageously almost flat and takes the form of a flat fan contained in the sectional plane P. The intersection of this beam with the sectional plane P has the appearance of an angular segment of which the vertex is merged with the source 11, and of which the angle at the vertex Δ, called angular aperture of the fan beam, is advantageously between 13° and 30°, preferably between 15° and 25°.

The thickness of the beam measured on the detector 12 is less than 30 mm, advantageously less than 20 mm.

The center of rotation O is situated at the intersection of the horizontal sectional plane P and the vertical axis of rotation Z-Z. The center of rotation O is situated at a fixed position between the source 11 and the detector 12, at a distance L1 from the source 11. The detector 12 is situated at a distance L2 from the source 11. The ratio L1/L2 is advantageously between 0.75 and 0.9, preferentially between 0.8 and 0.9.

The length L2 is advantageously less than 2 meters, more advantageously less than 1.5 meters, preferentially between 1.1 meters and 1.4 meters.

This configuration makes it possible to inspect a wide range of tires of which the size varies almost from single to double, while keeping the relative positions of the source 11, of the detector 12 and of the center of rotation O identical. Thus, this device makes it possible to inspect small tires of private passenger vehicles, for example tires with a width of 155 mm, an internal diameter of 380 m and an external diameter of 520 mm. Furthermore, it also makes it possible to inspect significantly larger tires, for example tires of all-terrain vehicles with a width of 355 mm, an internal diameter of 585 mm and an external diameter of 900 mm.

The combination of an angular aperture Δ of between 15° and 25° with a ratio L1/L2 of between 0.8 and 0.9 is particularly advantageous, because it results in a robust, sensitive, fast and compact inspection device.

Furthermore, because of the fixed position of the center of rotation O, there is no need to proceed with a complex calibration of the device when tire size changes occur.

Prejudices have had to be overcome to imagine being able to inspect, with a fixed center of rotation O, a wide range of tires. In effect, the prior art devices, and notably the one disclosed by EP0471096A1, vary the position of the center of rotation as a function of the size of the tires to be inspected, notably to avoid having the rotationally driven tire come to strike the detector, the latter having to pass inside the tire during the inspection cycle. Now, contrary to all expectation, it is possible to retain a fixed center of rotation O to cover a wide range of tires, provided that the angular aperture of the beam Δ is between 13° and 30° and the ratio L1/L2 is between 0.75 and 0.9.

Figure 5:
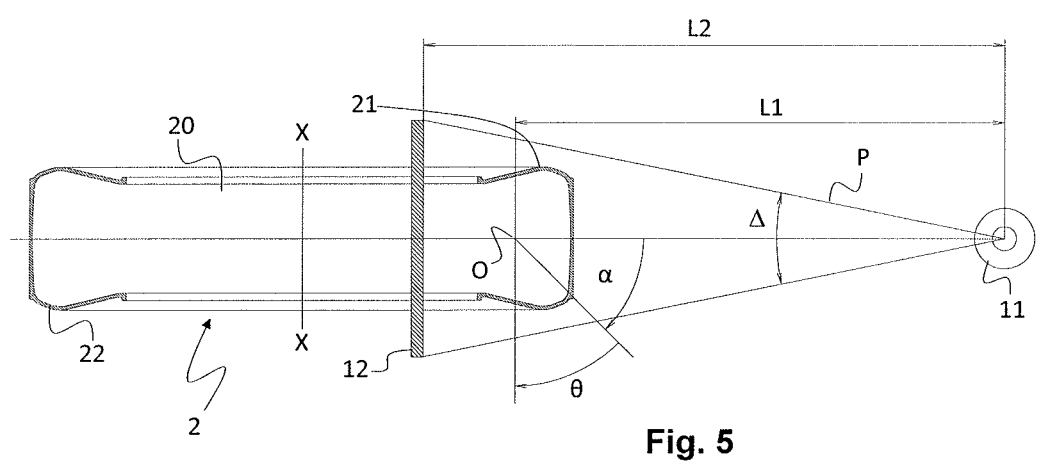

FIG. 5 illustrates a first intermediate position obtained by rotation of the tire 2 by an angle θ about the section of cover 21 and, more specifically by rotation of the tire 2 about the vertical axis of rotation passing through the center of rotation O situated, according to this example, inside the section of cover 21 to be tomographied. According to the invention, the tire 2 is rotated by an angle θ about the vertical axis of rotation passing through the center of rotation O, by passing the detector 12 inside the tire 2 through the central internal zone 20 of the tire, the beam being intercepted by the detector 12 after passing through all of the section of cover 21.

Figure 6:
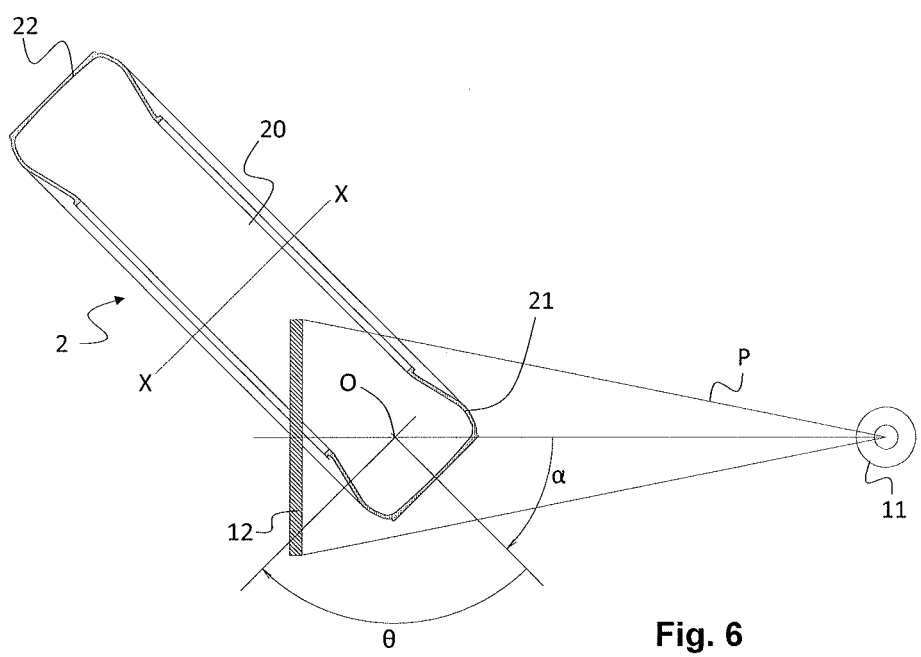
Figure 7:
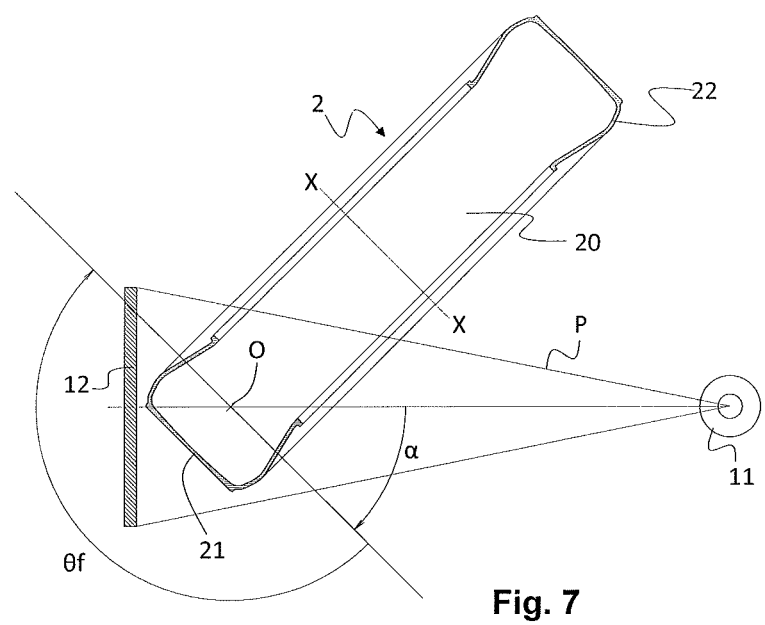

FIG. 6 shows a subsequent intermediate position obtained by continuing the continuous rotation of the tire 2 about the vertical axis of rotation passing through the center of rotation O situated inside the section of cover 21 to be tomographied, still by passing the detector 12 inside the tire 2 through the central internal zone 20. During the image acquisition phase, the rotation of the tire 2 in the vertical position about the section of cover 21 tomographied in the sectional plane P is performed preferentially with a total angular excursion θf of between 180° and 200°. FIG. 7 illustrates the final position that is thus obtained with such an angular excursion for the rotational movement of the tire 2 about the section of cover 21 to be tomographied.

Now, preference will be given to the use of a linear detector over a matrix detector. This is because a linear detector is more compact and can therefore more easily pass inside the central internal zone 20 of the tire, notably when the tire is of smaller size. Furthermore, a linear detector is simpler and less costly to implement than a matrix detector. Finally, the acquisition time of a linear detector is advantageously shorter compared to a matrix detector. By way of example, for the inspection of a private passenger vehicle tire, it will notably be possible to use a linear detector 512 mm wide, comprising for example 2560 pixels 0.2 mm wide. For the inspection of a larger size tire, for example a truck tire, it will notably be possible to use a linear detector 1024 mm wide, for example comprising 2560 pixels 0.4 mm wide or even 5120 pixels 0.2 mm wide.

The linear detector should be sufficiently wide to intercept all of the fan beam. Thus, for example, in the case where the beam has an angular aperture Δ equal to 20°, and in the case where the distance L2 separating the source from the detector is equal to 1.3 meters, the width of the detector should be at least equal to $2 \times L2 \times tg(\Delta/2) = 459$ mm. In practice, a detector of slightly greater width than this minimum, for example 512 mm wide in this example, is chosen.

It has been seen that the handling carriage also makes it possible to modify the azimuth of the cover to be tomographied without modifying the position of the tire within the actual chamber, by virtue of the means 32 for rotationally driving the tire about its axis. Thus, it is possible to perform a tomographic inspection of multiple sections of covers in a reduced cycle time. It is for example possible to perform the tomography of a first section of cover of an outbound angular travel corresponding to the rotation of the revolving plate in a first direction and, at the end of this first angular travel, after rotation of the tire about its axis, to perform the tomography of a second section of cover over the return angular travel corresponding to the rotation of the revolving plate in the reverse direction to the first direction.

The inspection device is thus suitable for acquiring absorption measurements for a given section of cover from a number of directions considered in the horizontal sectional plane P. For this, a relative movement is introduced between the tire and the source-detector assembly relative to an axis of rotation at right angles to the horizontal sectional plane, such that, during the image acquisition phase, the source-detector assembly and the tire perform a rotation relative to one another about this axis of rotation by following a trajectory exhibiting a predetermined angular excursion, advantageously between 180° and 360° and preferentially equal to 180°. During the rotation, it is thus possible to acquire, in the sectional plane, different series of measurements of the absorption of the radiation by the section of cover of the tire. These measurements are stored and used to reconstruct, using a suitable computational algorithm, a tomographic image of the section of cover of the tire, which constitutes a transversal cross section of the cover of the tire in the plane P.

The above description has been given in relation to an exemplary embodiment in which the tire is held vertically relative to the sectional plane which, for its part, is horizontal. It would equally be possible to be able to provide for the tire to be held horizontal (i.e. with its axis arranged vertically) during the inspection cycle without in any way departing from the scope of the present invention, the sectional plane then being positioned vertically. In this case, the tire is preferentially immobile during the inspection cycle and the source-detector assembly is driven in rotation according to an axis of rotation at right angles to the sectional plane, i.e. according to a horizontal axis of rotation.

Generally, in the case where the tire is immobile during the implementation of an inspection cycle, the invention can be implemented regardless of the position of the tire. Similarly, in the case where the source-detector assembly is immobile during the inspection cycle, the invention can be implemented regardless of the position of this assembly.

Moreover, the arrangement of the invention, consisting in passing the detector inside the central internal zone of the tire during the inspection cycle, so as to always have a single section of cover between the source and the detector passed through by the radiation intercepted by the detector and to thus be able to tomography a single section of cover of the tire simultaneously, is particularly advantageous with regard to one possible variant, which would consists in passing the radiation source inside the tire, with the detector, for its part, being positioned outside of the tire. In effect, in addition to the bulk constraints, the arrangement of the invention with the detector passing through the central internal zone of the tire during the inspection cycle is particularly advantageous in that it makes it possible for the detector to be thus placed as close as possible to the section of cover tomographied during the inspection cycle and thereby makes it possible to obtain a good image quality. Furthermore, to obtain a good image quality, it is not only necessary for the detector to be placed as close as possible to the cover of the tire, but also for the source to be far enough away from the detector to limit the blurring and the angular aperture of the beam intercepted by the detector. In practice, the source and the detector should advantageously be more than 1 meter apart and the detector should advantageously be situated at less than 100 mm from the cover of the tire. These conditions are particularly easy to satisfy with the source-detector arrangement according to the invention, whereas they would be impossible to produce by passing the source inside the central internal zone of the tire.

The invention claimed is:

1. A device for inspecting a tire to enable representation of tomographic images of sections of a cover of said tire, comprising:
    a source-detector assembly including:
    a source of ionizing radiation located outside of said tire configured for emitting the radiation in the form of a divergent beam; and
    a detector configured for receiving said radiation after said radiation passes through at least a part of said tire;
    wherein said source-detector assembly positions said detector facing said source at a predetermined distance L2 from said source and being situated opposite said source relative to at least one section of said cover of said tire;
    a holder for said tire configured for holding said tire between said source and said detector with an axis (X-X) of said tire extending parallel to a sectional plane (P) passing through a focus (F) of said source and said detector, at least one of said holder of said tire and said source-detector assembly are configured and operable for being moved by a rotational movement relative to one another about an axis of rotation (Z-Z) at right angles to said sectional plane (P), and said axis of rotation intersects with said sectional plane and passes through a center of rotation (O) situated in the source-detector assembly between said source and said detector at a predetermined distance L1 from said source, said device being configured and operable such that, during an inspection cycle of a tire, said detector is arranged at least partly in an open central, internal zone of an annular shape of said tire;
    wherein intersection of said divergent beam with said sectional plane exhibits an angular aperture (Δ) of between 13° and 30°, wherein said center of rotation is positioned in said source-detector assembly in a fixed manner between said source and said detector such that the ratio L1/L2 is between 0.75 and 0.9, whereby said device is configured and operable for inspecting tires of different dimensions by keeping constant the relative positions of said source, of said detector and of said center of rotation.

2. The device as claimed in claim 1, wherein said center of rotation (O) is situated inside said section of said cover of said tire.

3. The device as claimed in claim 1, wherein said angular aperture is between 15° and 25°.

4. The device as claimed in claim 1, wherein said ratio L1/L2 is between 0.8 and 0.9.

5. The device as claimed in claim 1, wherein said distance L2 is less than 2 meters.

6. The device as claimed in claim 1, wherein said source of ionizing radiation is a source of X-rays and said detector is configured to detect the x-rays.

7. The device as claimed in claim 6, wherein said source of radiation is an X-ray tube of a voltage less than 250 kV.

8. The device as claimed in claim 6, wherein said detector is a linear or matrix detector.

9. The device as claimed in claim 1, wherein said relative rotational movement between said source-detector assembly and said tire is a continuous movement.

10. The device as claimed in claim 1, wherein at least one of said holder for rotationally driving said tire or said source-detector assembly is configured to rotate about said axis of rotation (Z-Z) over an angular excursion range extending over at least 180°.

11. The device as claimed in claim 1, wherein said tire is arranged such that the axis (X-X) of said tire belongs to said sectional plane passing through the focus of said source and said detector.

12. The device as claimed in claim 1, further comprising said source is equipped with a collimator configured such that the radiation is emitted in the form of a planar beam contained in said sectional plane (P).

13. The device as claimed in claim 1, wherein said holder is configured to hold said tire in a vertical orientation while an axis of said tire is horizontal and said sectional plane (P) is horizontal.

14. The device as claimed in claim 1, wherein said holder is configured to hold said tire in a horizontal orientation while an axis of said tire is vertical and said sectional plane (P) is vertical.

15. A method for inspecting a tire by providing representation of tomographic images of sections of a cover of said tire, comprising:
    providing a tire to be inspected and a source-detector assembly comprising a source of ionizing radiation configured to emit a radiation to said tire in the form of a divergent beam, and a detector for detecting said radiation;
    said method comprising the steps of:
    configuring said source-detector assembly such that said detector is aligned with said source at a predetermined distance L2 from said source, and locating said source and said detector such that said source and said detector are respectively situated on respective axially opposite sides of said cover of said tire, with an axis (X-X) of said tire extending parallel to a sectional plane (P) passing through a focus (F) of said source and said detector;
    during a tire inspection cycle, generating a relative rotational movement between said tire and said source-detector assembly about an axis of rotation (Z-Z) at right angles to said sectional plane (P), wherein said axis of rotation intersects with said sectional plane passing through a center of rotation (O) situated in the source-detector assembly between said source and said detector at a predetermined distance L1 from said source, while also passing said detector, at least partly, inside a central internal zone of said tire during said rotational movement;
    during said inspection cycle, said detector is configured and operable to measure the absorption of said radiation passing through at least one section of said cover along said sectional plane (P); and
    said method further comprising:
    causing intersection of said divergent beam with said sectional plane to exhibit an angular aperture (Δ) of between 13° and 30°, whereas said center of rotation is positioned in said source-detector assembly in a fixed manner between said source and said detector such that a ratio L1/L2 is between 0.75 and 0.9, whereby it is possible to inspect tires of different dimensions while keeping constant the relative positions of said source, of said detector and of said center of rotation.

* * * * *